(12) United States Patent
Izumi et al.

(10) Patent No.: US 11,521,842 B2
(45) Date of Patent: Dec. 6, 2022

(54) MASS SPECTROMETRIC DATA ANALYSIS DEVICE AND ANALYSIS METHOD

(71) Applicant: SHIMADZU CORPORATION, Kyoto (JP)

(72) Inventors: Hideaki Izumi, Kyoto (JP); Shigeki Kajihara, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 940 days.

(21) Appl. No.: 16/321,130

(22) PCT Filed: Jul. 29, 2016

(86) PCT No.: PCT/JP2016/072278
§ 371 (c)(1),
(2) Date: May 15, 2019

(87) PCT Pub. No.: WO2018/020652
PCT Pub. Date: Feb. 1, 2018

(65) Prior Publication Data
US 2019/0267222 A1    Aug. 29, 2019

(51) Int. Cl.
*H01J 49/00*     (2006.01)
*G06N 20/00*     (2019.01)
(Continued)

(52) U.S. Cl.
CPC ........ *H01J 49/0036* (2013.01); *G01N 27/623* (2021.01); *G01N 33/57484* (2013.01); *G06N 20/00* (2019.01)

(58) Field of Classification Search
CPC ............... G01N 27/62; G01N 27/622; G01N 33/57484; G06N 20/00; G16H 10/40;
(Continued)

(56) References Cited

U.S. PATENT DOCUMENTS 7,542,959 B2 *  6/2009  Barnhill ............... G06K 9/6269
706/20
2002/0024009 A1    2/2002  Baranov
(Continued)

FOREIGN PATENT DOCUMENTS

CA    2 575 641 A1    3/2006
EP    1 778 856 A2    5/2007
(Continued)

OTHER PUBLICATIONS

First Office Action dated Dec. 1, 2020 from the China National Intellectual Property Administration in Machine Chinese Patent Application No. 201680089696.7.
(Continued)

*Primary Examiner* — Roy Y Yi
*Assistant Examiner* — Geoffrey T Evans
(74) *Attorney, Agent, or Firm* — Sughrue Mion, PLLC

(57) ABSTRACT

To improve the reliability of mutual diagnosis in a cancer determination by machine learning, m/z values of ions originating from tumor markers or similar substances used in other related tests are stored in a particular m/z-value database. A spectrum information filtering section deletes signal intensities at the m/z values stored in the particular m/z-value database from a large number of mass spectra classified by the presence or absence of cancer. Using the data which remain after the deletion as training data, a training processor obtains training-result information and stores it in a training result database. A judgment processor similarly deletes signal intensities at the predetermined m/z values from mass spectrum data obtained for a target sample to be judged. Then, based on the training-result information stored in the training-result database, the judgment processor determines whether the target sample should be classified into a cancerous group or non-cancerous group.

10 Claims, 3 Drawing Sheets

(51) Int. Cl.
*G01N 33/574* (2006.01)
*G01N 27/623* (2021.01)

(58) Field of Classification Search
CPC ..... G16H 50/20; G16H 50/70; H01J 49/0036; G16B 40/10; G16B 40/20
See application file for complete search history.

(56) References Cited

U.S. PATENT DOCUMENTS

| | | |
|---|---|---|
| 2008/0025591 A1 | 1/2008 | Bhanot et al. |
| 2008/0187207 A1 | 8/2008 | Bhanot et al. |
| 2009/0042229 A1 | 2/2009 | Folkman et al. |
| 2010/0213368 A1 | 8/2010 | Wang et al. |

FOREIGN PATENT DOCUMENTS

| | | | |
|---|---|---|---|
| JP | 2008-508538 A | 3/2008 | |
| JP | 2014-044110 A | 3/2014 | |
| JP | 2015-49055 A | 3/2015 | |
| KR | 10-2007-0043868 A | 4/2007 | |
| WO | 2006/022895 A2 | 3/2006 | |
| WO | WO-2006022895 A2 * | 3/2006 | ......... G01N 33/6872 |
| WO | WO-2016187671 A1 * | 12/2016 | ............. G06N 3/084 |

OTHER PUBLICATIONS

International Search Report for PCT/JP2016/072278 dated Oct. 18, 2016 (PCT/ISA/210).
International Search Report for PCT/JP2016/072278 dated Oct. 18, 2016 (PCT/ISA/237).
Communication dated Jun. 5, 2020 from European Patent Office in EP Application No. 16910555.8.
Third Office Action dated Apr. 6, 2022 issued for the corresponding Chinese Application No. 201680089696.7.
First Office Action dated Sep. 27, 2022 issued for the corresponding European Patent Application No. 16910555.8.

* cited by examiner

MASS SPECTROMETRIC DATA ANALYSIS DEVICE AND ANALYSIS METHOD

This application is a National Stage of International Application No. PCT/JP2016/072278 filed Jul. 29, 2016.

TECHNICAL FIELD

The present invention relates to a mass spectrometric data analysis device and analysis method for analyzing data acquired with a mass spectrometer. More specifically, it relates to a mass spectrometric data analysis device and analysis method useful for the testing of and judgment on samples in various areas, such as the diagnosis and testing of specific kinds of diseases, the true-false testing of the origin of farm and marine products or similar products, as well as the judgment on fake drugs, fake notes or similar articles.

BACKGROUND ART

In recent years, with the rapid advancement of mass spectrometric techniques, attempts have been made to diagnose specific kinds of diseases, such as cancer, by analyzing data acquired by a mass spectrometric analysis of biological samples (such as blood, urine, saliva or a piece of biological tissue) collected from subjects. For example, Patent Literature 1 discloses a technique proposed by the applicant and associates, in which a technique of statistical machine learning called dPLRM (dual Penalized Logistic Regression Machine) is applied to mass spectrum data collected by performing a mass spectrometric analysis on biological samples, to test each biological sample for cancer. The use of such a technique of statistical machine learning in place of a commonly used multivariate analysis enables the extraction of an extremely miniscule difference from an enormous amount of complex data. Based on such a difference, whether a sample is cancerous or uncancerous can be determined with a higher level of accuracy.

Statistical machine learning has already been used, or has begun to be used, in various areas, such as voice recognition, character recognition, face recognition or other types of image recognition as well as judgment on the authenticity of various products, in addition to the disease diagnosis as described earlier. Algorithms for such statistical machine learning can be roughly divided into supervised learning and unsupervised learning, of which supervised learning is more commonly used. In a normal procedure of supervised machine learning, a large number of pieces of data which have been classified into a plurality of groups are previously given as training data, from which the boundaries of those groups are to be learned. The result of this training is subsequently used as the basis for determining the group into which a piece of new data should be classified. For example, the plurality of groups in the device described in Patent Literature 1 are the group of cancer patients and that of healthy individuals (or non-cancer patients). In the following descriptions, supervised machine learning is simply called "machine learning".

In the previously described machine learning, if the new data to be tested is identical to one of the large number of pieces of training data, the task of pattern matching is easy and exact. However, in most cases, there are statistical errors, noise components and other undesirable factors which occur in the data acquisition process. Furthermore, if the samples are of biological origin, there is a comparatively significant amount of individual difference among the samples, and even the samples belonging to the same group may have a considerable amount of fluctuations in their data. In order to prevent the boundaries separating the groups from being affected by the fluctuations of the data, it is necessary to prepare training data which contain a sufficient number of pieces of information with a sufficient magnitude of fluctuations. In machine learning, it is normal to weigh the number of training data, the range of variation of the specimens from which training data are to be sampled, and other related factors in order to avoid the influences of such fluctuations of the data. Additionally, machine learning is normally carried out on the assumption that both the acquisition of the training data and that of the data to be tested are performed under the same data-acquisition conditions. Accordingly, the measurements for acquiring the data should be performed under the same conditions to the highest possible extent.

For the screening or clinical diagnosis of cancers or other serious diseases, a high level of correctness and reliability is naturally required. Therefore, the judgment results obtained by the previously described technique employing the combination of mass spectrometry and machine learning are normally used along with those obtained by other diagnostic methods, such as the marker test using a tumor marker as well as X-ray diagnostic imaging. MRI and other types of diagnostic imaging. Doctors or other medical experts comprehensively analyze those judgment results and make a conclusion. For the final judgment to be made on the basis of a plurality of judgment results in this manner, it is preferable that those judgment results be based on different factors. In other words, the judgment results should be highly independent of each other. The reason for this requirement is as follows: For example, consider the case of using two different techniques for the testing or judgment. If the two testing or judgment techniques are concerned with the same factor, a specimen which has been judged to be presumably cancerous by one of the techniques will inevitably be judged to be presumably cancerous by the other technique. In a practical sense, this does not mean that two different techniques have been used for the judgment.

For example, in the case of determining whether a specimen is cancerous or uncancerous based on differences between cancerous and uncancerous specimens extracted by machine learning using mass spectra acquired with a mass spectrometer, it is most likely that a change in the amount of ions originating from marker molecules which characterize the cancer is also included in the training result. A cancer determination based on such a training result cannot be considered as independent of a tumor-marker test which uses those marker molecules as the target. In such a situation, it is difficult to ensure the correctness or reliability of the diagnosis based on the combination of the two results.

Furthermore, due to various factors as will be hereinafter described, there is the case where a variation of the data which goes far beyond the range of normal fluctuations caused by individual differences among specimens occurs between the time of training phase and the time of judging phase, or the case where it is difficult to create the same data-acquisition conditions for both the training data and the data to be judged. Such situations contribute to a deterioration of the correctness of the judgment.

(1) During the process of cancer treatment, cancer patients are normally dosed with various types of anticancer drugs and other drugs. A change in biological tissue due to such a treatment occurs in the training data, and this change may be incorrectly recognized as a tissue change due to the cancer in the training phase.

(2) Contrary to case (1), a piece of data obtained from a patient dosed with a new type of anticancer drug may be judged on the basis of a training result obtained from training data which do not include any data of the new agent. If a peak originating from the new anticancer drug is incidentally located around a mass-to-charge ratio on the mass spectrum at which a difference between cancerous and uncancerous specimens occurs, the peak may be incorrectly judged to be a tissue change associated with the cancerous/uncancerous state. Similarly, if a peak originating from a mixed or foreign substance whose data is not included in the training data is included in the data subjected to the determination of the cancerous/uncancerous state, the peak may be incorrectly judged to be a tissue change associated with the cancerous/uncancerous state. In the case where an internal standard substance is added to the sample to be tested, a peak originating from the internal standard substance may also be incorrectly judged to be a tissue change associated with the cancerous/uncancerous state.

(3) The sampling of biological samples from cancer patients and healthy individuals as well as the measurement of those samples are normally performed in hospitals or similar medical institutions. It is difficult to conduct the sampling and measurement of samples by the same procedure and with the same level of quality in all medical institutions. Such a procedural or qualitative variation among different institutions may emerge in the form of a difference in signal intensities at specific mass-to-charge ratios and be incorrectly judged as a difference between the cancerous and uncancerous states.

As noted earlier, there may be a difference between the condition under which the data to be judged are acquired and the condition under which the training data are acquired. Furthermore, a variation which goes far beyond the range of normal fluctuations that occur due to the individual difference among specimens may occur in the specimens during the period of time from the acquisition of the training data to the acquisition of the data to be judged. In such cases, it is preferable to once more collect training data and perform machine learning using the newly acquired data. However, the task of once more collecting a large number of biological samples which fit the purpose and performing measurements on those samples requires an extremely large amount of time and labor. In many cases, such a task is practically impossible.

The problems described so far are most likely to arise from the particular fact that the samples are of biological origin. However, the same or similar problems can also occur in other areas that are not related to the disease diagnosis (or the like).

CITATION LIST

Patent Literature

Patent Literature 1: JP 2014-44110 A

SUMMARY OF INVENTION

Technical Problem

The present invention has been developed to solve the previously described problem. Its primary objective is to provide a mass spectrometric data analysis device and analysis method in which, even when a set of training data prepared for machine learning contain information that is also used in a different type of judgment technique, both the judgment by the machine learning and the judgment by the judgment technique different from the machine learning can be individually performed with a high degree of independence from each other so that the correctness and reliability of the entire judgment can be ensured.

The secondary objective of the present invention is provide a mass spectrometric data analysis device and analysis method in which, even when there is a difference between the condition under which the data to be judged are acquired and the condition under which the training data are acquired, or when a variation which may possibly constitute an interfering factor different from particular differences that contribute to the classification of specimens into a plurality of groups has occurred during the period of time from the acquisition of the training data to the acquisition of the data to be judged, a correct judgment can be made by machine learning without being affected by such a difference in the data-acquisition condition or variation as well as without requiring re-acquisition of the training data.

Solution to Problem

A mass spectrometric data analysis method according to the present invention developed for solving the primary and secondary objectives is a mass spectrometric data analysis method for classifying a target sample between a plurality of groups based on mass spectrum data acquired by performing a mass spectrometric analysis on the target sample, wherein the mass spectrum data is applied to training-result information obtained through executing predetermined machine learning using, as training data, a plurality of sets of mass spectrum data acquired by performing a mass spectrometric analysis on each of a plurality of samples classified into the plurality of groups, the method including:

a) a training-data filtering step including a process of deleting signal-intensity information or modifying the weighting of the signal-intensity information at one or more previously determined mass-to-charge ratios or within one or more previously determined mass-to-charge-ratio ranges for each of the plurality of sets of mass spectrum data given as the training data;

b) a training execution step including a process of creating training-result information by executing the machine learning using the training data processed in the training-data filtering step, and a process of storing the training-result information;

c) a target-data filtering step including, on mass spectrum data acquired for a target sample, a process equivalent to the process performed in the training-data filtering step; and d) a determination execution step including a process of determining which group the target sample belongs to among the plurality of groups, based on the mass spectrum data processed in the target-data filtering step and using the training-result information stored in the training execution step.

The first aspect of the mass spectrometric data analysis device according to the present invention developed for solving the primary and secondary problems, which is one device that embodies the previously described mass spectrometric data analysis method according to the present invention, is a mass spectrometric data analysis device for classifying a target sample between a plurality of groups from mass spectrum data acquired by performing a mass spectrometric analysis on the target sample, wherein the mass spectrum data is applied to training-result information obtained through executing predetermined machine learning using, as training data, a plurality of sets of mass spectrum data acquired by performing a mass spectrometric analysis on each of a plurality of samples classified into the plurality of groups, the device including:

a) a training-data filtering section for performing a process of deleting signal-intensity information or modifying the weighting of the signal-intensity information at one or more previously determined mass-to-charge ratios or within one or more previously determined mass-to-charge-ratio ranges for each of the plurality of sets of mass spectrum data given as the training data;

b) a training execution section for creating training-result information by executing the machine learning using the training data processed by the training-data filtering section, and for storing the training-result information;

c) a target-data filtering section for executing, on mass spectrum data acquired for a target sample, a process equivalent to the process performed by the training-data filtering section; and d) a determination execution section for determining which group the target sample belongs to among the plurality of groups, based on the mass spectrum data processed by the target-data filtering section and using the training-result information stored in the training execution section.

In the mass spectrometric data analysis method and analysis device according to the present invention, the mass spectrum data include mass spectrum data acquired with a commonly used single type of mass spectrometer, as well as $MS^n$ spectrum data with n being equal to or greater than two acquired with a triple quadrupole mass spectrometer. Q-TOF mass spectrometer, TOF-TOF mass spectrometer, ion trap mass spectrometer, ion trap time-of-flight mass spectrometer or other appropriate types of mass spectrometers.

In the mass spectrometric data analysis method and analysis device according to the present invention, the machine learning may be performed by any algorithm as long as it is a type of supervised machine learning. For example, a technique using a Bayesian estimation (e.g. dPLRM), a technique using a support vector machine (SVM), or a technique using a neural network may be employed, as described in Patent Literature 1.

In the mass spectrometric data analysis method and analysis device according to the present invention, mass spectrum data acquired by performing a mass spectrometric analysis on samples each of which belongs to a known group among a plurality of groups are given as training data. For example, if the analysis is aimed at determining whether or not a test subject is likely to have a cancer, there are only two groups, i.e. "cancerous" and "uncancerous". There is no limitation on the number of groups, although the range of available machine-learning algorithms changes depending on the number of groups. In general, if the given training data are labeled with groups, training-result information can be created by executing machine learning using the training data. In the case of the mass spectrometric data analysis method according to the present invention, the training-data filtering step is initially performed for each of the plurality of sets of mass spectrum data given as the training data, to delete the signal-intensity information at one or more previously determined mass-to-charge ratios or within one or more previously determined mass-to-charge-ratio ranges (i.e. to determine the signal-intensity information to zero), or to modify the weighting of the signal-intensity information (i.e. to increase or decrease the signal intensity by a predetermined percentage).

For example, the peaks which appear on a mass spectrum acquired by a normal mass spectrometric analysis that is not an $MS^n$ analysis typically originate from different compounds contained in a sample. Accordingly, deleting the signal-intensity information at a specific mass-to-charge ratio on a mass spectrum or decreasing the signal intensity at the mass-to-charge ratio means preventing the content of that specific compound in the sample from being reflected or involved in the training-result information or making the content less likely to be reflected in the training-result information. Therefore, for example, when it is necessary to additionally use a different diagnostic method (e.g. a tumor-marker test) for cancer diagnosis as noted earlier while ensuring the independence of each judgment, the mass-to-charge ratio of an ion originating from the compound used as the tumor marker can be determined as a mass-to-charge ratio at which the signal-intensity information should be deleted or the signal intensity should be decreased.

As other examples, when it is necessary to remove influences of anticancer drugs or other drugs administered to patients, the mass-to-charge ratio of each ion originating from anticancer drugs or other drugs that may possibly be used for the treatment can be determined as a mass-to-charge ratio at which the signal-intensity information should be deleted or the signal intensity should be decreased. When it is necessary to remove influences of various compounds (foreign substances) that may possibly be mixed into samples during the process of sample collection or measurement execution, the mass-to-charge ratio of each ion originating from each assumed foreign substance can be determined as a mass-to-charge ratio at which the signal-intensity information should be deleted or the signal intensity should be decreased. Possible examples of such foreign substances include the raw material of a container used for temporarily storing a sample, a plasticizer contained in the raw material, as well as a release agent and other additives used in the manufacturing of the container. Other possible examples of the foreign substances include a standard sample used in the calibration of the mass spectrometer, as well as the filler of a column, the mobile phase, its additive and other related substances in the case where the sample is preprocessed with a column or similar device. If the large number of mass spectrum data used as the training data have been acquired with different devices, a mass-to-charge-ratio range within which a considerable variation in detection sensitivity occurs due to the instrumental errors of the devices may be determined as a mass-to-charge-ratio range within which the signal-intensity information should be deleted or the signal intensity should be decreased.

In the process of deleting signal-intensity information or decreasing signal intensities at the mass-to-charge ratios or mass-to-charge-ratio ranges of ions originating from various compounds mentioned earlier, not only the molecular ion of each compound itself but also various other kinds of ions originating from or influenced by that compound may also be included in the ions whose signal-intensity information should be deleted or whose signal intensity should be decreased.

Specifically, it is preferable that the ions whose signal-intensity information should be deleted or whose signal intensities should be decreased additionally include a monovalent ion or multivalent ion of the compound of interest, or an ion produced from the compound by the addition or desorption of alkaline metal, halogen, water, various chemically-modifying groups or the like. It is also preferable to consider the influences of isotopes in the calculation of the mass-to-charge ratios at which the signal-intensity information should be deleted or the signal intensities should be decreased. Not only an ion originating from the very compound of interest, such as a tumor marker, but also an ion originating from a different compound which will be derived from the compound of interest, such as a metabolite of the compound of interest or a different in-vivo compound which will be affected by the compound of interest during the metabolic process, may also be included in the ions whose signal-intensity information should be deleted or whose signal intensities should be decreased.

In the training execution step, training-result information is created by executing predetermined machine learning using, as the training data, the mass spectrum data which have undergone the partial deletion of the spectrum information or other necessary operations in the training-data filtering step in the previously described manner. The training-result information is a set of information to be used for determining which group an unknown sample belongs to among a plurality of groups. The obtained training-result information is compiled into a database and stored in a storage device or similar location. In this database, the training-result information is related to information which shows, for example, the mass-to-charge ratios that have been deleted in the filtering process. Accordingly, for example, the content of the specific compounds whose spectrum information has been removed in the previously described manner will not be reflected in the training-result information.

For the determination of the group into which a target sample should be classified, a mass spectrometric analysis is performed on the target sample to acquire mass spectrum data for that compound. Subsequently, a process equivalent to the process performed in the training-data filtering step is performed on those mass spectrum data in the target-data filtering step. Thus, the data to be judged also undergo the previously described process of deleting the signal-intensity information or decreasing the signal intensities at or within the mass-to-charge ratios or mass-to-charge-ratio ranges of the ions originating from the specific compounds. In the determination execution step, the group into which the target compound should be classified among the plurality of groups is determined based on the processed mass spectrum data for the target sample, using the training-result information which has been stored in the previously described manner. If a target sample taken from a test subject has been classified into the "cancerous" group, it is concluded that the test subject presumably has a cancer.

As just described, influences of the presence or absence of specific compounds are eliminated in both the training phase based on the training data, i.e. the process of creating the training-result information, and the judgment phase for the data to be judged. Therefore, the determination on the classification can be performed without being affected by the presence or absence of those specific compounds. For example, when the mass-to-charge ratio of an ion originating from a compound used as a tumor marker is determined as the mass-to-charge ratio at which the signal-intensity information should be deleted or the signal intensity should be decreased, the classification of a target sample is determined based on mass spectrum data acquired for that target sample regardless of whether or not the compound used as the tumor marker is contained in the target sample. Accordingly, the determination on the classification, i.e. the judgment on the possibility of the presence of a cancer, will be more independent of the judgment in the tumor-marker test, so that a more reliable diagnosis can be made by combining those determination.

As described earlier, there are various compounds that may possibly be mixed into samples due to various factors, such as the sampling conditions, preprocessing conditions and measurement conditions. However, if the spectrum information related to all those compounds is deleted from mass spectrum data, it becomes more likely that the spectrum information of one or more compounds which must be observed will also be deleted with the unnecessary information. Therefore, it is preferable to narrow down the compounds to those which truly need to be deleted or which are most likely to be undesirably mixed into samples, according to the actual sampling conditions, preprocessing conditions, measurement conditions and other related factors, and to delete spectrum information of ions originating from those compounds from mass spectrum data.

As described earlier, in the mass spectrometric data analysis method according to the present invention, the mass-to-charge ratio at which the signal-intensity information should be deleted from the mass spectrum data or the signal intensity should be decreased in the training phase and the judging phase may be either the mass-to-charge ratio of an ion originating from a compound which may possibly have direct and adverse influences on the judgement by the present analysis method, or the mass-to-charge ratio of an ion originating from a compound which has no direct influences on the judgement by the present analysis method but should preferably be prevented from being reflected in the judgment result.

Thus, one mode of the mass spectrometric data analysis method according to the present invention is a mass spectrometric data analysis method, where the group into which the target sample is classified among the plurality of groups is determined in combination with a determination result obtained by a technique different from the previously-described analysis method, and one or more mass-to-charge ratios or mass-to-charge-ratio ranges of an ion originating from one or more compounds as a target of a measurement or test used in the different technique is determined as the one or more previously determined mass-to-charge ratios or mass-to-charge-ratio ranges.

As a specific example, the different technique may be a technique using a specific compound as a marker for a measurement or test, such as a tumor-marker test mentioned earlier or a lipid-marker test, in which case the mass-to-charge ratio or mass-to-charge-ratio range of an ion originating from the compound used as the marker and/or a metabolite of the compound and/or an in-vivo molecule influenced in the metabolic process may be determined as the one or more previously determined mass-to-charge ratios or mass-to-charge-ratio ranges.

In another mode of the mass spectrometric data analysis method according to the present invention, the mass-to-charge ratio of an ion originating from one or more compounds for which a significant difference in signal intensity on a mass spectrum is expected to occur between the training phase based on the training data and the judgment phase for a target sample, or a mass-to-charge-ratio range having a predetermined width including the aforementioned mass-to-charge ratio, is determined as the one or more previously determined mass-to-charge ratios or mass-to-charge-ratio ranges.

As a specific example, the sample may be a sample derived from a living organism, in which case the mass-to-charge ratio of an ion originating from one or more compounds, or a mass-to-charge-ratio range having a predetermined width including the aforementioned mass-to-charge ratio, may be determined as the one or more previously determined mass-to-charge ratios or mass-to-charge-ratio ranges, where the one or more compounds are selected from: a drug which is administered or may possibly be administered to the living organism; a metabolite of the drug; an in-vivo molecule which is influenced in a metabolic process; a standard substance which may possibly remain in the sample; and a compound which may possibly be mixed into the sample in a sampling, preprocessing or measurement process.

The mass-to-charge ratio of the aforementioned ion originating from one or more compounds for which a significant difference in signal intensity on a mass spectrum is expected to occur between the training phase based on the training data and the judgment phase for a target sample may be a mass-to-charge ratio extracted by a statistically analyzing process.

As described earlier, the first aspect of the mass spectrometric data processing device according to the present invention includes the filtering section for deleting spectrum information or modifying its weighting in a given set of training data according to predetermined conditions, and the training execution section for performing machine learning based on the processed training data. In order to perform the judgment of a target sample, the training-result information based on the training data after the filtering process only needs to be available.

Thus, the second aspect of the mass spectrometric data analysis device according to the present invention, which is one device that embodies the previously described mass spectrometric data analysis method according to the present invention, is a mass spectrometric data analysis device for classifying a target sample between a plurality of groups from mass spectrum data acquired by performing a mass spectrometric analysis on the target sample, wherein the mass spectrum data is applied to training-result information obtained through executing predetermined machine learning using, as training data, a plurality of sets of mass spectrum data acquired by performing a mass spectrometric analysis on each of a plurality of samples classified into the plurality of groups, the device including:

a) a training-result information storage section for storing training-result information created by executing the machine learning using, as training data, a set of data obtained through a filtering process performed for each of a plurality of sets of mass spectrum data originally given as the training data, the filtering process including deletion of signal-intensity information or modification of the weighting of the signal-intensity information at one or more previously determined mass-to-charge ratios or within one or more previously determined mass-to-charge-ratio ranges b) a target-data filtering section for executing, for mass spectrum data acquired for a target sample, the filtering process performed on the training data in the creation of the training-result information; and c) a determination execution section for determining which group the target sample belongs to among the plurality of groups, based on the mass spectrum data filtered by the target-data filtering section and using the training-result information stored in the training-result information storage section.

The training-result information storage section may be part of the hardware components constituting the analysis device. The minimum requirement is that the training-result information can be accessed and used. Accordingly, for example, the training-result information storage section may be located on a computer network accessible through the Internet or similar communication network.

Advantageous Effects of Invention

According to the mass spectrometric data analysis method and analysis device of the present invention, the task of classifying a target sample can be performed after deleting unwanted spectrum information or peak information from an enormous amount of mass spectrum data previously collected as training data. i.e. after removing the influences of such spectrum information or peak information. Therefore, for example, a judgment result which is highly independent of a tumor-marker test can be obtained by removing information concerning the tumor markers used in the tumor-marker test in both the training phase and the judging phase. Consequently, more appropriate information can be provided for doctors or other medical experts so that they can make a diagnosis with a higher degree of reliability.

In some cases, a change in data-acquisition conditions or related conditions can occur between the time of the collection of the training data and that of the collection of the data to be judged due to various factors, such as the influences of therapeutic drugs, the need for the addition of an internal standard sample to target samples, or the possibility that various compounds used in the collection or measurement of samples are mixed into the samples. Even in such cases, it is possible to appropriately classify target samples using an enormous amount of already collected training data, by removing spectrum information at mass-to-charge ratios or within mass-to-charge-ratio ranges which will be affected by the change in the conditions. Even when various problems related to the acquisition of the training data or that of the data to be judged are detected at a later point in time, a satisfactory judgment can be made by analyzing the influences of those problems and removing spectrum information at the mass-to-charge ratios or within mass-to-charge-ratio ranges which are thereby affected. Thus, the important data can be utilized without being wasted.

The task of collecting an enormous amount of mass spectrum data for the training data requires a huge amount of time and labor. The present invention does not require re-collecting an enormous amount of mass spectrum data when, for example, there are various kinds of markers whose influences need to be individually removed from the judgement; what is necessary is to merely change the training and judgment conditions for each marker. Thus, the present invention reduces the time and labor for the task of collecting mass spectrum data for the training data.

If the amount of training data is enormously large, the machine learning based on the training data often requires a computing time that can reach several hours or even tens of hours. This problem can be addressed by preparing a list of candidates of the mass-to-charge ratios or mass-to-charge-ratio ranges which should be excluded or whose weighting should be changed, obtaining a set of training-result information for each candidate by carrying out the machine learning corresponding to that candidate, and storing the obtained results. When a target sample is to be judged, an appropriate set of training-result information can be selected and used for the judgment. This enables the judgment on a target sample to be more quickly made.

DESCRIPTION OF EMBODIMENTS

One embodiment of a cancer diagnosis assistance device using a mass spectrometric analysis device for carrying out a mass spectrometric data analysis method according to the present invention is hereinafter described with reference to the attached drawings.

Figure 1:
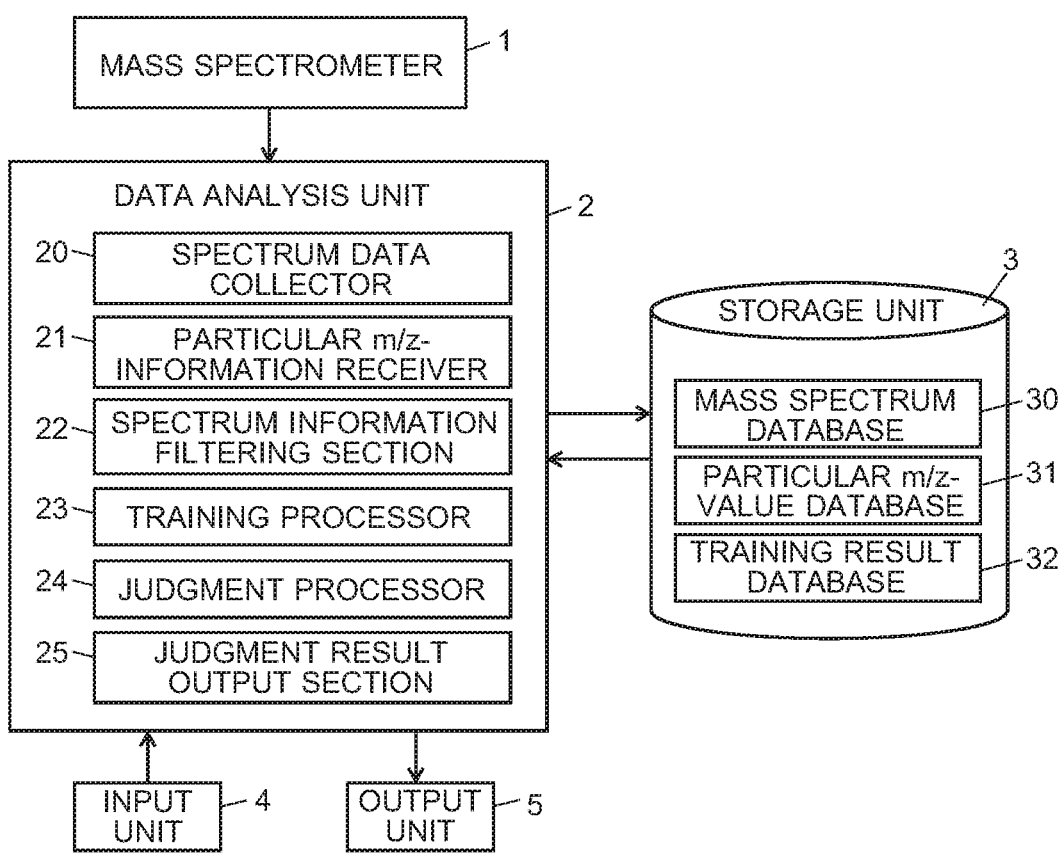
FIG. 1 is a schematic configuration diagram of a cancer diagnosis assistance device according to one embodiment of the present invention.
Figure 2:
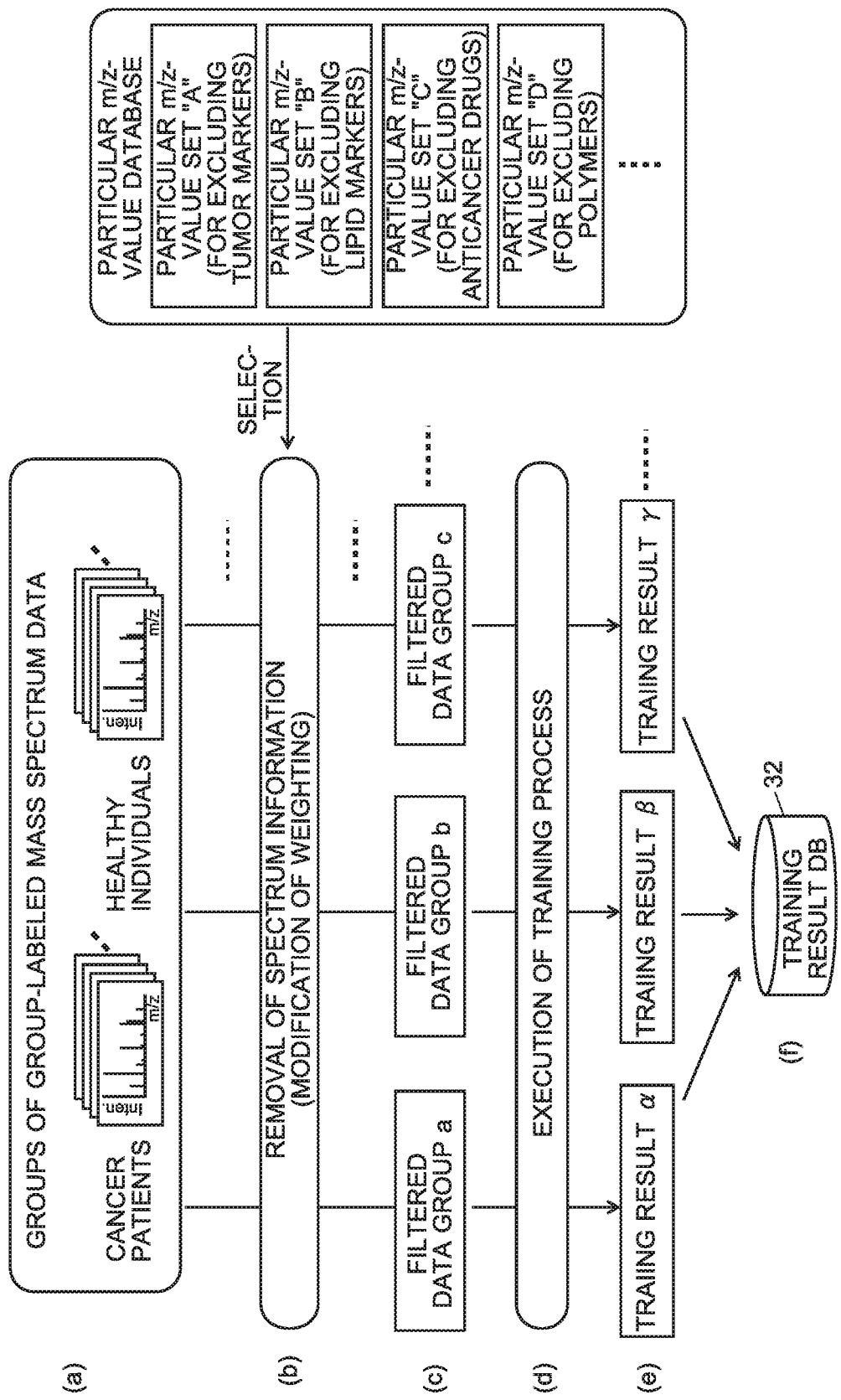
FIG. 2 is a diagram illustrating the operation in the training phase based on training data in the cancer diagnosis assistance device according to the embodiment.
Figure 3:
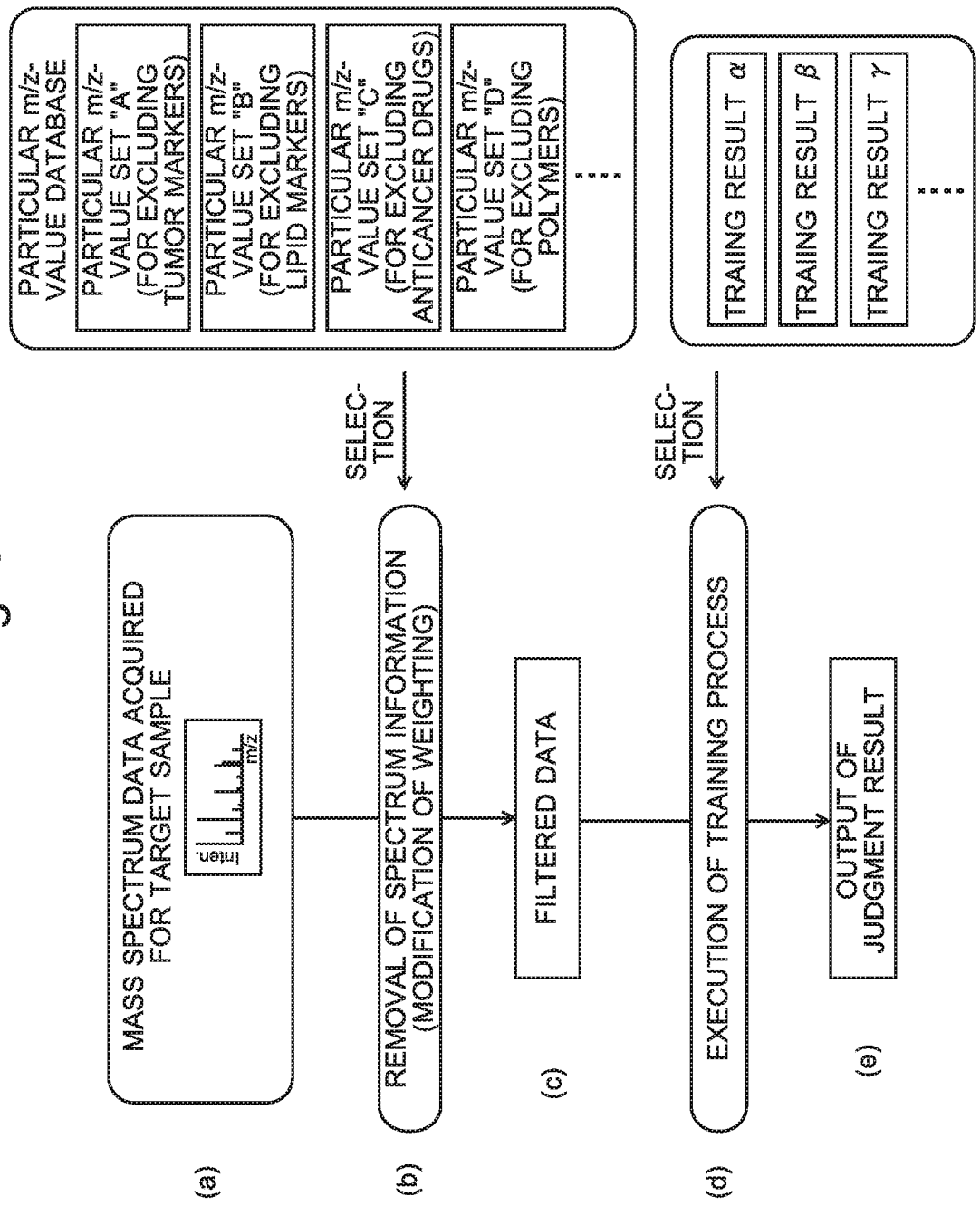
FIG. 3 is a diagram illustrating the operation of the judging phase for a target sample in the cancer diagnosis assistance device according to the embodiment.

FIG. 1 is a schematic configuration diagram of the cancer diagnosis assistance device according to the present embodiment. FIG. 2 is a diagram illustrating the operation in the training phase based on training data in the cancer diagnosis assistance device according to the embodiment. FIG. 3 is a diagram illustrating the operation of the judging phase for a target sample in the cancer diagnosis assistance device according to the embodiment.

The cancer diagnosis assistance device according to the present embodiment includes: a mass spectrometer 1 for performing a mass spectrometric analysis on a sample to acquire mass spectrum data; a data analysis unit 2 for executing an analytical process using mass spectrum data acquired with the mass spectrometer 1; a storage unit 3 in which databases (DBs) recording various kinds of data to be used for the analytical process are stored; an input unit 4 for allowing users to enter information (and the like) necessary for the analytical process; and a display unit 5 for displaying analysis results or other kinds of information.

The data analysis unit 2 includes a spectrum data collector 20, particular m/z-information receiver 21, spectrum information filtering section 22, training processor 23, judgment processor 24 and judgment result output section 25 as its functional blocks. In the storage unit 3, a mass spectrum database 30, particular m/z-value database 31 and training result database 32 are stored.

The data analysis unit 2 is actually a personal computer or more sophisticated computer. Each of the aforementioned functions can be realized by executing, on the computer, a dedicated data analysis software program previously installed on the same computer. The functions of the data analysis unit 2 may be shared by two or more computers. Specifically, the training function (which will be described later) and the judging function for target samples can be assigned to a different computer. In machine learning, the amount of calculation required for the training is normally far greater than required for the judgment. Accordingly, the efficiency of the entire processing can be improved by using a high-performance computer as the computer for the training, and a normal type of personal computer as a computer for the judgment. The storage unit 3 does not need to be a hardware device contained in or connected to a computer, for example, it may be a storage device located on a computer system that is accessible through the Internet or similar communication network, i.e. a storage device in the cloud computing.

The mass spectrometer 1 may employ any type of ionization method or mass separation method as long as it can acquire mass spectrum data (including MS' spectrum data) for a sample of biological origin, such as a small piece of biological tissue, blood, urine or saliva. For example, a quadrupole mass spectrometer or time-of-flight mass spectrometer equipped with a PESI ion source as described in Patent Literature 1 can be used.

Characteristic operations in the cancer diagnosis assistance device according to the present embodiment are hereinafter described with reference to FIGS. 2 and 3.

For the present cancer diagnosis assistance device to be available for the judgment on whether or not a test subject is likely to have a cancer, it is necessary to previously construct the training result database 32 and store it in the storage unit 3. The construction of the training result database 32 requires a set of training data labeled with their respective groups. There are two groups to be considered in the present case: "cancerous" group and "non-cancerous (uncancerous)" group. If there are two or more possible types of cancer for the same kind of biological tissue, the "cancerous" group may be subdivided into a plurality of groups corresponding to those types of cancer. For example, it is commonly known that renal cell carcinoma can be classified into different types, such as the clear cell type or granule cell type. Each of those types can be handled as a separate group.

In order to provide a set of training data labeled with their respective groups, a large number of biological samples respectively collected from a large number of cancer patients who has been proved to have cancer by a pathological diagnosis (or the like), as well as a large number of biological samples collected from a large number of healthy individuals who has been proved to have no cancer, are individually subjected to a mass spectrometric analysis with the mass spectrometer 1 to acquire a set of mass spectrum data for each sample. Thus, for example, a large number of sets of mass spectrum data labeled as the "cancerous" group, and a large number of sets of mass spectrum data labeled as the "uncancerous" group, are obtained (see (a) in FIG. 2).

The spectrum data collector 20 in the data analysis unit 2 receives each set of mass spectrum data from the mass spectrometer 1 and creates vector data (or matrix data) in the form of a vector which holds peak information (mass-to-charge ratios and signal intensities) obtained by performing a peak-detecting operation on the mass spectrum. The vector data are classified into groups (i.e. labeled) and stored in the mass spectrum database 30 in the storage unit 3.

The vector data based on mass spectra and stored in the mass spectrum database 30 do not need to be based on mass spectrum data acquired with a single mass spectrometer 1. They may be based on mass spectrum data acquired with two or more mass spectrometers (which should preferably be the same type of mass spectrometers).

On a mass spectrum obtained for a sample, a plurality of peaks which respectively correspond to a plurality of compounds contained in the sample are normally observed. However, not all peaks are useful for the task of classifying the target compound by machine learning.

For example, in many cases, a cancer patient is dosed with anticancer drugs and other drugs for cancer treatment, and there are various kinds and combinations of drugs which can be used for that purpose. Spectrum information of ions originating from those drugs and their metabolites, as well as in-vivo substances which may possibly be altered in the metabolic process, can adversely influence the correct classification of the target samples. Additionally, the compounds used in the materials of the containers or tools used for the sampling, preprocessing, measurement or other tasks for samples, as well as additives used for those materials, may also be mixed into the samples. Spectrum information of ions originating from those compounds (which can be regarded as foreign substances in a broad sense) can also adversely influence the correct classification of the target samples. Therefore, it is preferable to exclude, from the training result, spectrum information related to the ions originating from those drugs, or ions originating from those foreign substances.

Furthermore, for example, if information relating to the content of a compound used for a tumor-marker test (marker molecule), its metabolite or other related substances is included in the training result, the correlation between the judgment based on the training result and the judgment in the tumor-marker test will be considerably high, so that these judgments can no longer be considered to be sufficiently independent of each other. In order to ensure independence of a plurality of judgments which will be used in combination, it is necessary to exclude, from the training result, information related to compounds which will be the targets in other diagnostic or testing methods.

Accordingly, in the cancer diagnosis assistance device according to the present embodiment, the mass-to-charge ratios or mass-to-charge-ratio ranges which are of particular interest in the training phase, i.e. which should be excluded from mass spectrum data (whose signal-intensity values should be zero) or within which the weighting of the signal intensity should be decreased, are previously registered in the particular m/z-value database 31. As will be described later, there are an extremely large number of kinds of compounds which are of particular interest. Therefore, in the present embodiment, those compounds to be registered in the particular m/z-value database 31 are grouped into a plurality of sets each of which includes mass-to-charge-ratio values or mass-to-charge-ratio ranges originating from a plurality of compounds of particular interest. Users can select one or more groups through the input unit 4 and specify how the spectrum information (i.e. signal-intensity information) at the mass-to-charge ratios included in the selected groups should be handled, e.g. whether the information should be removed or its weighting should be modified, as well as how much the weighting should be changed in the case of modifying the weighting.

In the example shown in FIG. 2, there are four groups to be registered in the particular m/z-value database 31: "Set A" for excluding tumor markers, "Set B" for excluding lipid markers, "Set C" for excluding anticancer drugs, and "Set D" for excluding polymers. "Set A" includes the mass-to-charge-ratio values of ions originating from α-FP, which is commonly used as a tumor marker for liver cancer, CA15-3, which is commonly used as a tumor marker for the screening of breast cancer, and other similar compounds. "Set B" includes the mass-to-charge-ratio values of ions originating from lipoproteins and other similar compounds. "Set C" includes the mass-to-charge ratios of ions originating from folinic acid, fluorouracil, oxaliplatin and other representative anticancer drugs. "Set D" includes the mass-to-charge ratios of ions originating from vinyl chloride, vinylidene chloride, diphenyl carbonate and other high-molecular compounds contained in measurement tools (or the like) which may possibly come in contact with samples, as well as their thermolysis products.

The particular m/z-value database 31 may be previously created by the manufacturer that provides hardware or software products of the present device, or users themselves may create the database. It is also possible for the manufacturer to create a basic version of the particular m/z-value database 31 and allow users to modify this database 31 as well as add information to or delete information from the database as needed. Specific examples of the compounds that may be included in the particular nm/z-value database 31 will be described later in detail.

A user operating the input unit 4 selects a group or groups (or one specific compound, etc.) in the particular m/z-value database 31, as described earlier. Upon receiving the selection, the particular m/z-information receiver 21 reads the information corresponding to the selection from the particular m/z-value database 31 and sets it in the spectrum information filtering section 22. For example, if the user has designated two groups "Set A" and "Set C" as the spectrum information that should be excluded, the particular m/z-information receiver 21 reads the entire mass-to-charge-ratio-value information included in the two groups "Set A" and "Set C" in the particular m/z-value database 31, and sets the information in the spectrum information filtering section 22.

The spectrum information filtering section 22 sequentially reads each set of data (e.g. the vector data mentioned earlier) showing the peak information corresponding to one set of mass spectrum data from the mass spectrum database 30, and deletes the signal-intensity information (i.e. determines the intensity values to zero) corresponding to the mass-to-charge ratios or mass-to-charge-ratio ranges determined by the particular m/z-information receiver 21, or decreases the weight of the signal-intensity information corresponding to those mass-to-charge ratios or mass-to-charge-ratio ranges, for example, by multiplying each intensity value by a predetermined factor which is less than one. In other words, a filtering process for deleting spectrum information at specific mass-to-charge ratios or within specific mass-to-charge-ratio ranges, or decreasing intensity values at specific mass-to-charge ratios or within specific mass-to-charge-ratio ranges, is performed on all mass spectrum data labeled with the groups (see (b) in FIG. 2). If, for example, a peak originating from a tumor marker included in "Set A" is present on an acquired mass spectrum, the peak will be effectively removed by the filtering process. For example, a filtered data group "a" is obtained by excluding spectrum information at specific mass-to-charge ratios or within specific mass-to-charge-ratio ranges included in "Set A" and "Set C" from vector data based on each set of mass spectrum data (see (c) in FIG. 2).

Subsequently, the training processor 23 reads the filtered data (e.g. data group "a" mentioned earlier) and carries out machine learning using those data to obtain training result a (see (d) and (e) in FIG. 2). The obtained training result a is stored in the training result database 32 (see (f) in FIG. 2). In the case of using dPLRM as the machine-learning algorithm, the training-result information takes the form of a set of optimized dPLRM parameters which give a predictive probability. This algorithm is commonly known, as described in Patent Literature 1 or other related documents. Therefore, no detailed explanation is given in the present description. Needless to say, a technique different from dPLRM may also be used as the machine-learning algorithm. In that case, a specific form of training-result information corresponding to the used technique will be obtained.

As described earlier, the training data handled in the training processor 23 does not contain the spectrum information which has been effectively removed by the previously described filtering process. Therefore, the spectrum information effectively removed by the filtering process is not reflected in the training-result information stored in the training result database 32. For example, in the previous example, neither the signal-intensity information at the mass-to-charge ratios of the ions originating from the tumor markers included in "Set A" nor the signal-intensity information at the mass-to-charge ratios of the ions originating from the anticancer drugs included in "Set C" will be reflected in the training-result information.

In the cancer diagnosis assistance device according to the present embodiment, two or more sets of different training-result information can be created from the same vector data stored in the mass spectrum database 30, by appropriately selecting, from the particular m/z-value database 31, a different group to be excluded or by appropriately changing the mass-to-charge ratios or mass-to-charge-ratio ranges included in the selected group. The obtained sets of training-result information can be stored in the training result database 32.

For example, in addition to the training result a which is obtained by selecting "Set A" and "Set C" as the groups to be excluded, other training results may also be stored in the training result database 32, such as training result 3 prepared by directly using, as the training data, the vector data stored in the mass spectrum database 30 without performing any filtering process, and/or training result y prepared by using training data from which the ions originating from the compounds included in the "Set D" group have been excluded. Thus, various patterns of training-result information which are available for cancer diagnosis can be prepared from the same collection of mass spectrum data and stored beforehand in the training result database 32 as needed by the user. A wide variety of training-result information can be prepared by changing the combinations of the mass-to-charge ratios to be included in the groups which should be excluded.

When a cancer determination for a biological sample collected from a test subject is to be performed, a mass spectrometric analysis of the target sample with the mass spectrometer 1 is initially performed to acquire mass spectrum data. Then, the spectrum data collector 20 reads the measured mass spectrum data, collects peak information, and creates vector data representing the peak information in the form of a vector (see (a) in FIG. 3).

The user operating the input unit 4 selects, for example, a group or groups of mass-to-charge ratios which should be excluded from the mass spectrum data. Upon receiving the selection, the particular m/z-information receiver 21 determines the mass-to-charge ratios or mass-to-charge-ratio ranges to be excluded in the spectrum information filtering section 22. This operation is the same as in the training phase. The spectrum information filtering section 22 deletes spectrum information corresponding to the mass-to-charge ratios or mass-to-charge-ratio ranges determined by the particular m/z-information receiver 21, or decreases the weight of the intensity values corresponding to those mass-to-charge ratios or mass-to-charge-ratio ranges, for example, by multiplying each intensity value by a predetermined factor which is less than one. Consequently, a set of filtered data is obtained (see (b) and (c) in FIG. 3).

The judgment processor 24 reads, from the training result database 32, the training-result information based on the training data from which the selected groups (or the like) have been removed. In other words, the judgment processor 24 retrieves training-result information obtained in the training phase under the same filtering conditions as currently applied in the judging process. Using the retrieved training-result information, the judgment processor 24 calculates the probability that the filtered data belong to the "cancerous" group or "uncancerous" group, and determines which group the data should belong to (see (d) in FIG. 3). The judgment result output section 25 displays the judgment result in a predetermined form on the screen of the display unit 5. For example, the probability of being cancerous or non-cancerous can be graphically displayed (see (e) in FIG. 3).

As described to this point, in the cancer diagnosis assistance device according to the present embodiment, for example, when training-result information is created using training data, spectrum information of ions originating from tumor markers is excluded from the training data. Similarly, when a cancer determination for a target sample is to be carried out, the spectrum information of the ions originating from the same tumor marker is excluded beforehand from the data obtained for the target sample. Therefore, the content of the tumor marker does not influence the result of the cancer determination. Thus, a sufficiently high degree of independence is ensured between the judgment by the cancer diagnosis assistance device according to the present embodiment and the judgment by a separately performed tumor-marker test, so that a highly reliable cancer diagnosis can be achieved based on those judgment results.

Hereinafter listed are examples of substances (compounds) which should preferably be excluded from mass spectrum data for cancer determination in the cancer diagnosis assistance device according to the present embodiment.

[1] Substances which are used in other methods for the diagnosis or testing of cancer, or selected as a target in those methods, and therefore, should preferably be excluded in both the training phase and the judging phase by the present device in order to ensure independence of each individual judgment:

Examples of tumor markers which are commonly used for the diagnosis or testing of cancer include α-FP, CA15-3, CA27-29, CA19-9, CA-125, CEA, SCC, CYFRA and Pro-GRP. Spectrum information of ions originating from the molecules of those tumor markers or ions originating from metabolites of those tumor markers should preferably be excluded from mass spectrum data. Other substances which are used as tumor markers or are considered to be potentially usable as tumor markers include calcitonin, calretinin, CD34, CD99, CD117, chromogranin, chromosome 3,7,17, 9p21, cytokeratin, desmin, EMA, GFAP, GCFP-15, HMB-45, hCG, immunoglobulin, inhibin, keratin, lymphocyte marker, MART-1, Myo D1, MSA, neurofilament, NSE, PLAP, prostate-specific antigen, PTPRC (CD45), S100 proteins, SMA, synaptophysin, thyroglobulin, thyroid, transcription factor-1, tumor M2-PK, and vimentin. Those substances may also be excluded from mass spectrum data as with the tumor markers as needed.

[2] Substances that may possibly cause a difference in the measurement conditions (or the like) between the training phase and the judging phase and should preferably be excluded in both the training phase and the judging phase:

[2-1] In the diagnosis of cancer or other diseases, the disease treatment itself may constitute a biasing factor due to specific substances the use of which cause a difference in the measurement conditions between the training phase and the judging phase. For example, the substances (anticancer drugs) listed below are often used solely or in combination in the cancer treatment. Spectrum information of ions originating from those substances and their metabolites should preferably be excluded from mass spectrum data as needed.

folinic acid (leucovorin) <formula: $C_{20}H_{23}N_7O_7$, molecular weight: 473.44> fluorouracil (5-FU) <formula: $C_4H_3FN_2O_2$, molecular weight: 130.077> tegafur <formula: $C_8H_9FN_2O_3$, molecular weight: 200.16> uracil <formula: $C_4H_4N_2O_2$, molecular weight: 112.09> gimeracil <formula: $C_5H_4ClNO_2$, molecular weight: 145.54> oteracil potassium <formula: $C_4H_2KN_3O_4$, molecular weight: 195.17>

FdUMP <formula: $C_9H_{12}FN_2O_8P$, molecular weight: 326.172345> flucytosine <formula: $C_4H_4FN_3O$, molecular weight: 129.09> doxifluridine (5-DFUR) <formula: $C_9H_{11}FN_2O_5$, molecular weight: 246.19> capecitabine <formula $C_{15}H_{22}FN_3O_6$, molecular weight: 359.35> levamisole <formula: $C_{11}H_{12}N_2S$, molecular weight: 204.292> levofolinate <formula: $C_{20}H_{21}N_7O_7 \cdot Ca$, molecular weight: 473.44+Ca> cisplatin <formula $Cl_2H_6N_2Pt$, molecular weight: 300.05> vinblastine <formula: $C_{46}H_{58}N_4O_9$, molecular weight: 810.975 (+$SO_4$ sulfate)> cyanocobalamine <formula: $C_{63}H_{88}CoN_{14}O_{14}P$, molecular weight: 1355.38> doxorubicin (adriacin) <formula: $C_{27}H_{29}NO_{11}$, molecular weight: 543.52 (579.98 (hydrochloride))> doxorubicin <formula: $C_{27}H_{29}NO_{11}$, molecular weight: 543.52> epirubicin <formula: $C_{27}H_{29}NO_{11}$, molecular weight: 543.519 (579.98 (hydrochloride))> pemetrexed <formula: $C_{20}H_{21}N_5O_6$, molecular weight: 427.41/formula: $C_{20}H_{19}N_5Na_2O_6 \cdot 7H_2O$, molecular weight: 597.49> methotrexate <formula: $C_{20}H_{22}N_8O_5$, molecular weight: 454.44> allopurinol <formula: $C_5H_4N_4O$, molecular weight: 136.112> temozolomide <formula: $C_6H_6N_6O_2$, molecular weight: 194.151> bleomycin <formula: $C_{55}H_{84}N_{17}O_{21}S_3$, molecular weight: 1415.551> mithramycin <formula: $C_{52}H_{76}O_{24}$, molecular weight: 1085.15> mitomycin C <formula: $C_{15}H_{18}N_4O_5$, molecular weight: 334.327> etoposide <formula: $C_{29}H_{32}O_{13}$, molecular weight: 588.557> irinotecan <formula: $C_{33}H_{38}N_4O_6$, molecular weight: 586.678 (677.185 (hydrochloride))> camptothecin <formula: $C_{20}H_{16}N_2O_4$, molecular weight: 348.352> cyclophosphamide <formula: $C_7H_{15}Cl_2N_2O_2P \cdot H_2O$, molecular weight: 279.10> ifosfamide <formula: $C_7H_{15}Cl_2N_2O_2P$, molecular weight: 261.1> thiotepa <formula: $C_6H_{12}N_3PS$, molecular weight: 189.2> busulfan <formula: $C_6H_{14}O_6S_2$, molecular weight: 246.304> nimustine <formula: $C_9H_{13}ClN_6O_2$, molecular weight: 272.69> nimustine hydrochloride <formula: $C_9H_{14}Cl_2N_6O_2$, molecular weight: 309.15> ranimustine <formula: $C_{10}H_{18}ClN_3O_7$, molecular weight: 327.71> carmustine <formula: $C_5H_9Cl_2N_3O_2$, molecular weight: 214.05> lomustine <formula: $C_9H_{16}ClN_3O_2$, molecular weight: 233.695> streptozocin <formula: $C_8H_{15}N_3O_7$, molecular weight: 265.221> semustine <formula: $C_{10}H_{18}ClN_3O_2$, molecular weight: 247.72> dacarbazine <formula: $C_6H_{10}N_6O$, molecular weight: 182.18> mesna <formula: $C_2H_5NaO_3S_2$, molecular weight: 164.181> vincristine <formula: $C_{46}H_{56}N_4O_{10}$, molecular weight: 824.958> chlorambucil <formula: $C_{14}H_{19}Cl_2NO_2$, molecular weight: 304.212> melphalan <formula: $C_{13}H_{18}Cl_2N_2O_2$, molecular weight: 305.2>

<Nitrogen Mustard Series>

N,N-bis(2-chloroethyl)ethylamine (HN-1) <formula: $CH_3CH_2N(CH_2CH_2Cl)_2$, molecular weight: 170.08>

N,N-bis(2-chloroethyl)methylamine (HN-2, mechlorethamine) <formula: $CH_3N(CH_2CH_2Cl)_2$, molecular weight: 156.054> tris(2-chloroethyl)amine (HN-3) <formula: $(CH_2CH_2Cl)_3N$, molecular weight: 204.52> docetaxel <formula: $C_{43}H_{53}NO_{14}$, molecular weight: 807.879> paclitaxel <formula: $C_{47}H_{51}NO_{14}$, molecular weight: 853.906> gemcitabine <formula: $C_9H_{11}F_2N_3O_4$, molecular weight: 263.198> cytarabine <formula: $C_9H_{13}N_3O_5$, molecular weight: 243.22> daunorubicin <formula: $C_{27}H_{29}NO_{10}$, molecular weight: 527.52 (563.99 (hydrochloride))> mitoxantrone <formula $C_{22}H_{28}N_4O_6$, molecular weight: 444.481> zosuquidar <formula: $C_{32}H_{31}F_2N_3O_2$, molecular weight: 527.61> actinomycin <formula: $C_{62}H_{86}N_{12}O_{16}$, molecular weight: 1255.42> prednisolone <formula: $C_{21}H_{28}O_5$, molecular weight: 360.45> asparaginase <formula: $C_{1377}H_{2208}N_{382}O_{442}S_{17}$, molecular weight: 31731.9> mercaptopurine <formula: $C_5H_4N_4S$, molecular weight: 152.177> oxaliplatin (L-OHP) <formula: $C_8H_{14}N_2O_4Pt$, molecular weight: 397.2858> carboplatin (CBDCA) <formula: $C_6H_{12}N_2O_4Pt$, molecular weight: 371.249> levamisole <formula: $C_{11}H_{12}N_2S$, molecular weight: 204.292> bevacizumab <formula: $C_{1034}H_{1591}N_{273}O_{338}S_6$ ($C_{2235}H_{3413}N_{585}O_{678}S_{16}$), molecular weight: 149 kDa> cetuximab <formula: $C_{6484}H_{10042}N_{1732}O_{2023}S_{36}$, molecular weight: 145781.6> panitumumab <formula: $C_{6398}H_{9878}N_{1694}O_{2016}S_{48}$, molecular weight: 147 kDa>

[2-2] Some substances may possibly be mixed into samples as foreign substances in a measurement or other tasks and cause a difference in the measurement conditions between the training phase and the judging phase. Examples of such substances include thermolysis products of high-molecular compounds used as the material of measurement tools, such as a container for holding a sample or a sample plate, as well as the monomer, dimer and trimer of raw materials which remain due to insufficient purification or for other reasons. Representative examples of commonly known high-molecular compounds (polymers) include vinyl chloride, vinylidene chloride, carbonyl chloride, diphenyl carbonate, bisphenol A/PTBT (p-t-butylphenol), phenol and styrene as well as the monomer, dimer and trimer of any of those polymers. Spectrum information of ions originating from those substances should also preferably be excluded from mass spectrum data as needed.

[2-3] There may also be influences of the contamination by plasticizers contained in the materials of the aforementioned measurement tools (or the like). Representative examples of commonly known plasticizers include phthalates, dioctyl phthalate, diisononyl phthalate, diisodecyl phthalate, dibutyl phthalate, adipates, dioctyl adipate, diisononyl adipate, trimellitates, trioctyl trimellitate, polyesters, phosphates, tricresyl phosphate, citrate, ATBC (acetyl tributyl citrate), epoxidized vegetable oil, ESBO (epoxidized soybean-oil) ELSO (epoxidized linseed-oil), sebacate, azelate, maleate, and benzoate. Spectrum information of ions originating from those substances should also preferably be excluded from mass spectrum data as needed.

[2-4] There may also be influences of the contamination by release agents used in the manufacturing of the aforementioned measurement tools (or the like) as well as modified products of those agents. Representative examples of commonly known release agents include vegetable oil, silicone series, and fluorine resin series. Spectrum information of ions originating from those substances should also preferably be excluded from mass spectrum data as needed.

[2-5] There may also be influences of the contamination by standard substances or reagents used for the calibration of mass spectrometers or other purposes, as well as other substances added to those standard substances or reagents. Examples of such substances include polyethylene glycol, NaTFA, NaI, CsI, papaverine, p-nitrophenol, reserpine, angiotensin and bradykinin. Spectrum information of ions originating from those substances should also preferably be excluded from mass spectrum data as needed.

[2-6] There may also be influences of the contamination by the residue of various substances, such as a substance used for the preprocessing of samples or an eluate from a column used for the separation of sample components. Examples of such substances include chloroform, acetonitrile and siloxane. Spectrum information of ions originating from those substances should also preferably be excluded from mass spectrum data as needed.

[2-7] Though this is not due to foreign substances, a difference in the measurement conditions between the training phase and the judging phase easily occurs in mass spectrum data within a mass-to-charge-ratio range where the performance of the used device is likely to fluctuate or deteriorate, such as the data obtained at mass-to-charge ratios near the upper and lower limits of the measurable range. Accordingly, for example, spectrum information of ions included within specific mass-to-charge-ratio areas near the upper and lower limits of the measurable range should also preferably be excluded from mass spectrum data as needed.

For the task of effectively excluding spectrum information due to the various aforementioned factors from mass spectrum data, users can use one of the following techniques to predict spectrum information whose influences should be decreased, and specify the spectrum information (e.g. mass-to-charge-ratio values) to be effectively removed based on the prediction.

[A] An actual measurement on a real sample, an actual measurement on a standard sample (or the like), an actual measurement on a blank sample (e.g. a sample which consists of only a solvent), or an actual measurement on other kinds of samples is performed to acquire a mass spectrum which includes spectrum information whose influences should be decreased, and this mass spectrum is analyzed to identify spectrum information whose influences should be decreased. In this case, spectrum information whose mixture into the mass spectrum can actually be confirmed, or whose mixture can be confirmed as being likely to occur, will be effectively removed.

For the aforementioned analysis, commonly known techniques for multivariate analysis can be used, such as principal component analysis (PCA) or partial least squares (PLS). For example, even when there is no detailed information about specific metabolites, a peak or peaks which are highly correlated with a known mass-to-charge ratio can be extracted by the technique of multivariate analysis and be designated as the peaks to be removed. Such a correlation is not limited to the substances which are consumed or produced by metabolism; a change in the spectrum pattern due to an influence on ionization, such as an ion suppression associated with the presence of a specific peak, can also be extracted. Accordingly, a similar analysis can be used to analyze the influences of the addition of internal standard samples or presence of contaminants. Multivariate analysis can similarly be used to extract peaks which are highly correlated with other specific factors, such as the instrumental errors of devices or differences among institutions which carried out measurements. Such peaks can be considered to be easily affected by systematic errors, and therefore, may be designated as the peaks to be excluded.

[B] In some cases, one or more substances whose influences should be removed can be previously specified, as with the case where a tumor-marker test using a known tumor marker is carried out in combination with the judgment by the present device, or the case where anticancer drugs (or the like) which have been administered to the cancer patients (or the like) are previously known. In such cases, the mass-to-charge ratios of ions formed by specific reactions in the process of the ionization of the known substances or their metabolites into monovalent or multivalent ions should be calculated, inclusive of the influences of their isotopes, and spectrum information corresponding to the mass-to-charge ratios determined by the calculation should be excluded. Examples of the specific reactions include the addition or desorption of one or more electrons, addition or desorption of one or more atoms of hydrogen, addition or desorption of one or more atoms of alkaline metal (Na, K, Rb, Cs, Fr, etc.), addition or desorption of one or more atoms of other kinds of metal, addition or desorption of one or more atoms of halogen (F, Cl, Br, I, At, etc.), hydration, dehydration, as well as addition or desorption of one of the various chemically-modifying groups (e.g. sulphate group, acetic acid group or nitric acid group).

[C] A substance originally contained in a sample may be altered during its ionization into a monovalent or multivalent ion due to the addition (or the like) of a chemically-modifying group or metal atom which is a part of another substance originally contained in or additionally mixed into the sample or a metabolite of this substance. In view of such a possibility, the mass-to-charge ratios of ions resulting from the substance in question by addition reactions should be calculated, inclusive of the influences of their isotopes, and spectrum information corresponding to the mass-to-charge ratios determined by the calculation should be excluded. Examples of the addition reactions include the addition of one or more atoms of alkaline metal (Na, K, Rb, Cs, Fr, etc.), addition of one or more atoms of other kinds of metal, addition of one or more atoms of halogen (F, Cl, Br, I, At, etc.), hydration, as well as addition of one of the various chemically-modifying groups (e.g. sulphate group, acetic acid group or nitric acid group).

[D] A substance originally contained in a sample may be altered due to the desorption of a part of itself during its ionization into a monovalent or multivalent ion, due to the influences of another substance originally contained in or additionally mixed into the sample or a metabolite of this substance. In view of such a possibility, the mass-to-charge ratios of ions resulting from the substance in question by desorption reactions should be calculated, inclusive of the influences of their isotopes, and spectrum information corresponding to the mass-to-charge ratios determined by the calculation should be excluded. Examples of the desorption reactions include the desorption of one or more atoms of alkaline metal (Na, K, Rb, Cs, Fr, etc.), desorption of one or more atoms of other kinds of metal, desorption of one or more atoms of halogen (F, Cl, Br, I, At, etc.), dehydration, as well as desorption of one of the various chemically-modifying groups (e.g. sulphate group, acetic acid group or nitric acid group).

[E] If an ion originating from a substance which should be effectively removed is determined beforehand, the spectrum information within the entire mass-to-charge-ratio range having a predetermined width before and after the center of the mass-to-charge ratio of the ion in question should be excluded to allow for the influences of isotopes for the ion and a mass shift due to the device.

[F] In the determination on the necessity of the exclusion of spectrum information, the influence of the exclusion or inclusion of the spectrum information on the judgment result should be evaluated beforehand. The spectrum information should be excluded only when it can be confirmed that the exclusion yields a desired improvement in the evaluation.

Those methods [A] through [F] may be appropriately combined in determining which spectrum information should be excluded. If spectrum information which has no influence on the judgment result and does not truly need to be removed is removed, important spectrum information whose mass-to-charge ratios overlap those of the unwanted spectrum information may also be accidentally removed and cause a deterioration in the judgment accuracy. By limiting the target of the removal to such spectrum information that truly needs to be removed, it becomes easier to ensure the judgment accuracy.

The device may also be configured to allow for not only the exclusion of the spectrum information corresponding to specific mass-to-charge ratios or mass-to-charge-ratio ranges, but also the modification of the weighting, i.e. the relative magnitudes of the signal-intensity values, for one or more specific mass-to-charge ratios or mass-to-charge-ratio ranges. This configuration allows the weight on a mass-to-charge ratio related to a specific marker to be increased, rather than decreased, to make a judgment which places emphasis on that mass-to-charge ratio. For example, if a new marker molecule has been discovered, or if a substance which seems to be an unwanted mixture has been detected at a later point in time, the influence of the spectrum information of ions originating from such a substance on the already stored information in the database can be assessed by intentionally increasing the weight on the spectrum information in question.

The previously described embodiment is concerned with a cancer diagnosis assistance device employing a mass spectrometric data analysis device according to the present invention. The mass spectrometric data analysis device according to present invention is not limited to the diagnosis or judgment on a specific type of disease, such as cancer. It can also be used in various devices or application areas for determining which group an unknown sample should be classified into among a plurality of groups.

For example, the present invention can be used for the testing of whether or not the origin of farm products, marine products, animal products or any other kinds of products are from specific origins, or the testing of whether or not an expensive product is actually a similar inexpensive product (fake). It can also be used for the determination on the authenticity of drugs, bank bills or other kinds of industrial products, the discrimination between satisfactory and defective goods of industrial products, as well as the sorting of trash and waste.

It should be noted that the previously described embodiment is a mere example of the present invention. Any change, modification or addition appropriately made within the spirit of the present invention in any aspects other than those already described will also evidently fall within the scope of claims of the present application.

REFERENCE SIGNS LIST

1 . . . Mass Spectrometer
2 . . . Data Analysis Unit
20 . . . Spectrum Data Collector
21 . . . Particular m/z-Information Receiver
22 . . . Spectrum Information Filtering Section
23 . . . Training Processor
24 . . . Judgment Processor
25 . . . Judgment Result Output Section
3 . . . Storage Unit
30 . . . Mass Spectrum Database
31 . . . Particular m/z-Value Database
32 . . . Training Result Database
4 . . . Input Unit
5 . . . Display Unit

The invention claimed is:

1. A mass spectrometric data analysis method for classifying a target sample between a plurality of groups based on mass spectrum data acquired by performing a mass spectrometric analysis on the target sample, wherein the mass spectrum data is applied to training-result information obtained through predetermined machine learning using, as training data, a plurality of sets of mass spectrum data acquired by performing a mass spectrometric analysis on each of a plurality of samples classified into the plurality of groups, the method comprising:
  a) a training-data filtering step including a process of deleting signal-intensity information or modifying a weighting of the signal-intensity information at one or more previously determined mass-to-charge ratios or within one or more previously determined mass-to-charge-ratio ranges for each of the plurality of sets of mass spectrum data given as the training data;
  b) a training execution step including a process of creating training-result information by executing the machine learning using the training data processed in the training-data filtering step, and a process of storing the training-result information;
  c) a target-data filtering step including, on mass spectrum data acquired for a target sample, a process equivalent to the process performed in the training-data filtering step; and
  d) a determination execution step including a process of determining which group the target sample belongs to among the plurality of groups, based on the mass spectrum data processed in the target-data filtering step and using the training-result information stored in the training execution step, wherein the one or more previously determined mass-to-charge ratios or the one or more previously determined mass-to-charge-ratio ranges correspond to:

drugs used by a patient, metabolites of the drugs used by the patient, or compounds used in the materials of containers or tools used for sampling, preprocessing, measurement or other tasks for the sample.

2. The mass spectrometric data analysis method according to claim 1, wherein the one or more previously determined mass-to-charge ratios or the one or more previously determined mass-to-charge-ratio ranges correspond to drugs used by a patient or metabolites of the drugs used by the patient.

3. The mass spectrometric data analysis method according to claim 1, wherein the one or more previously determined mass-to-charge ratios or the one or more previously determined mass-to-charge-ratio ranges correspond to compounds used in the materials of containers or tools used for sampling, preprocessing, measurement or other tasks for the sample.

4. A mass spectrometric data analysis method for classifying a target sample between a plurality of groups based on mass spectrum data acquired by performing a mass spectrometric analysis on the target sample, wherein the mass spectrum data is applied to training-result information obtained through predetermined machine learning using, as training data, a plurality of sets of mass spectrum data acquired by performing a mass spectrometric analysis on each of a plurality of samples classified into the plurality of groups, the method comprising:

a) a training-data filtering step including a process of deleting signal-intensity information or modifying a weighting of the signal-intensity information at one or more previously determined mass-to-charge ratios or within one or more previously determined mass-to-charge-ratio ranges for each of the plurality of sets of mass spectrum data given as the training data;

b) a training execution step including a process of creating training-result information by executing the machine learning using the training data processed in the training-data filtering step, and a process of storing the training-result information;

c) a target-data filtering step including, on mass spectrum data acquired for a target sample, a process equivalent to the process performed in the training-data filtering step; and d) a determination execution step including a process of determining which group the target sample belongs to among the plurality of groups, based on the mass spectrum data processed in the target-data filtering step and using the training-result information stored in the training execution step, wherein:

the group into which the target sample is classified among the plurality of groups is determined in combination with a determination result obtained by a technique different from the previously-described analysis method; and one or more mass-to-charge ratios or mass-to-charge-ratio ranges used in the different technique is determined as the one or more previously determined mass-to-charge ratios or mass-to-charge-ratio ranges.

5. The mass spectrometric data analysis method according to claim 4, wherein:

the different technique is a technique using a specific compound as a marker for a measurement or test; and the mass-to-charge ratio or mass-to-charge-ratio range of an ion originating from the compound used as the marker and/or a metabolite of the compound and/or an in-vivo molecule influenced in the metabolic process is determined as the one or more previously determined mass-to-charge ratios or mass-to-charge-ratio ranges.

6. A mass spectrometric data analysis method for classifying a target sample between a plurality of groups based on mass spectrum data acquired by performing a mass spectrometric analysis on the target sample, wherein the mass spectrum data is applied to training-result information obtained through predetermined machine learning using, as training data, a plurality of sets of mass spectrum data acquired by performing a mass spectrometric analysis on each of a plurality of samples classified into the plurality of groups, the method comprising:

a) a training-data filtering step including a process of deleting signal-intensity information or modifying a weighting of the signal-intensity information at one or more previously determined mass-to-charge ratios or within one or more previously determined mass-to-charge-ratio ranges for each of the plurality of sets of mass spectrum data given as the training data;

b) a training execution step including a process of creating training-result information by executing the machine learning using the training data processed in the training-data filtering step, and a process of storing the training-result information;

c) a target-data filtering step including, on mass spectrum data acquired for a target sample, a process equivalent to the process performed in the training-data filtering step; and d) a determination execution step including a process of determining which group the target sample belongs to among the plurality of groups, based on the mass spectrum data processed in the target-data filtering step and using the training-result information stored in the training execution step, wherein:

a mass-to-charge ratio of an ion originating from one or more compounds for which a significant difference in signal intensity on a mass spectrum is expected to occur between a training phase based on the training data and a judgment phase for a target sample, or a mass-to-charge-ratio range having a predetermined width including the aforementioned mass-to-charge ratio, is determined as the one or more previously determined mass-to-charge ratios or mass-to-charge-ratio ranges.

7. The mass spectrometric data analysis method according to claim 6, wherein:

the sample is a sample derived from a living organism; and a mass-to-charge ratio of the ion originating from one or more compounds, or a mass-to-charge-ratio range having a predetermined width including the aforementioned mass-to-charge ratio, is determined as the one or more previously determined mass-to-charge ratios or mass-to-charge-ratio ranges, where the one or more compounds are selected from: a drug which is administered or may possibly be administered to the living organism; a metabolite of the drug; an in-vivo molecule which is influenced in a metabolic process; a standard substance which may possibly remain in the sample; and a compound which may possibly be mixed into the sample in a sampling, preprocessing or measurement process.

8. The mass spectrometric data analysis method according to claim 6, wherein:

the mass-to-charge ratio of the aforementioned ion originating from one or more compounds for which a significant difference in signal intensity on a mass spectrum is expected to occur between the training phase based on the training data and the judgment phase for a target sample is a mass-to-charge ratio extracted by a statistically analyzing process.

9. A mass spectrometric data analysis device for classifying a target sample between a plurality of groups from mass spectrum data acquired by performing a mass spectrometric analysis on the target sample, wherein the mass spectrum data is applied to training-result information obtained through executing predetermined machine learning using, as training data, a plurality of sets of mass spectrum data acquired by performing a mass spectrometric analysis on each of a plurality of samples classified into the plurality of groups, the device comprising:

a) a training-result information storage section for storing training-result information created by executing the machine learning using, as training data, a set of data obtained through a filtering process performed for each of a plurality of sets of mass spectrum data originally given as the training data, the filtering process including deletion of signal-intensity information or modification of a weighting of the signal-intensity information at one or more previously determined mass-to-charge ratios or within one or more previously determined mass-to-charge-ratio ranges; b) a target-data filtering section for executing, on mass spectrum data acquired for a target sample, the filtering process performed on the training data in a creation of the training-result information; and c) a determination execution section for determining which group the target sample belongs to among the plurality of groups, based on the mass spectrum data filtered by the target-data filtering section and using the training-result information stored in the training-result information storage section, wherein the one or more previously determined mass-to-charge ratios or the one or more previously determined mass-to-charge-ratio ranges correspond to:

drugs used by a patient, metabolites of the drugs used by the patient, or compounds used in the materials of containers or tools used for sampling, preprocessing, measurement or other tasks for the sample.

10. A mass spectrometric data analysis device for classifying a target sample between a plurality of groups from mass spectrum data acquired by performing a mass spectrometric analysis on the target sample, wherein the mass spectrum data is applied to training-result information obtained through executing predetermined machine learning using, as training data, a plurality of sets of mass spectrum data acquired by performing a mass spectrometric analysis on each of a plurality of samples classified into the plurality of groups, the device comprising:

a) a training-data filtering section for performing a process of deleting signal-intensity information or modifying a weighting of the signal-intensity information at one or more previously determined mass-to-charge ratios or within one or more previously determined mass-to-charge-ratio ranges for each of the plurality of sets of mass spectrum data given as the training data;

b) a training execution section for creating training-result information by executing the machine learning using the training data processed by the training-data filtering section, and for storing the training-result information;

c) a target-data filtering section for executing, on mass spectrum data acquired for a target sample, a process equivalent to the process performed by the training-data filtering section; and d) a determination execution section for determining which group the target sample belongs to among the plurality of groups, based on the mass spectrum data processed by the target-data filtering section and using the training-result information stored in the training execution section, wherein the one or more previously determined mass-to-charge ratios or the one or more previously determined mass-to-charge-ratio ranges correspond to:

drugs used by a patient, metabolites of the drugs used by the patient, or compounds used in the materials of containers or tools used for sampling, preprocessing, measurement or other tasks for the sample.

\* \* \* \* \*